United States Patent
Shin et al.

(10) Patent No.: US 9,971,048 B2
(45) Date of Patent: May 15, 2018

(54) DEVICE FOR DETECTING THERAPEUTIC PROTON BEAM EMITTED IN SCATTERING MODE

(71) Applicant: NATIONAL CANCER CENTER, Gyeonggi-do (KR)

(72) Inventors: Dong Ho Shin, Gyeonggi-do (KR); Me Young Kim, Gangwon-do (KR); Joo Young Kim, Gyeonggi-do (KR); Jae Man Son, Seoul (KR); Se Byeong Lee, Gyeonggi-do (KR); Young Kyung Lim, Gyeonggi-do (KR); Ui Jung Hwang, Gyeonggi-do (KR)

(73) Assignee: NATIONAL CANCER CENTER, Gyeonggi-do (KR)

( * ) Notice: Subject to any disclaimer, the term of this patent is extended or adjusted under 35 U.S.C. 154(b) by 0 days. days.

(21) Appl. No.: 15/108,984

(22) PCT Filed: Dec. 10, 2014

(86) PCT No.: PCT/KR2014/012117
§ 371 (c)(1),
(2) Date: Jun. 29, 2016

(87) PCT Pub. No.: WO2015/102255
PCT Pub. Date: Jul. 9, 2015

(65) Prior Publication Data
US 2016/0327659 A1    Nov. 10, 2016

(30) Foreign Application Priority Data

Dec. 31, 2013    (KR) .................. 10-2013-0169318

(51) Int. Cl.
*G01T 1/20* (2006.01)
*G01T 5/08* (2006.01)
(Continued)

(52) U.S. Cl.
CPC .............. *G01T 5/08* (2013.01); *A61N 5/1071* (2013.01); *A61N 5/1075* (2013.01); *G01T 1/22* (2013.01);
(Continued)

(58) Field of Classification Search
CPC ... G01T 1/1642; G01T 1/1644; G01T 1/2018; G01T 1/20; G01T 1/204
See application file for complete search history.

(56) References Cited

U.S. PATENT DOCUMENTS 4,292,537 A  *  9/1981  Davies .................. G01M 11/30
                                                                250/361 R
2015/0168563 A1*  6/2015  Lee ..................... A61N 5/1075
                                                                250/393

FOREIGN PATENT DOCUMENTS

JP      06-294871       10/1994
JP      2013-506823      2/2013
(Continued)

OTHER PUBLICATIONS

International Search Report and Written Opinion issued in PCT/KR2014/012117, dated Apr. 10, 2015.

*Primary Examiner* — David Porta
*Assistant Examiner* — Mamadou Faye
(74) *Attorney, Agent, or Firm* — Norton Rose Fulbright US LLP

(57) ABSTRACT

Disclosed is a proton beam detection device comprising a sensor having optical fiber of an arrangement structure capable of accurately and efficiently detecting proton dose distribution such as bragg peak, spread out bragg peak (SOBP) and symmetry of a therapeutic proton beam emitted in a scattering mode. The proton beam detection device, which detects a proton beam emitted from a proton beam source in a scattering mode, comprises a sensor having a plurality of detection modules including reference optical (Continued)

fiber and detection optical fiber having a length longer than the length of the reference optical fiber, the plurality of detection modules being diagonally arranged in the depth direction along which the proton beam emitted from the proton beam source proceeds.

3 Claims, 4 Drawing Sheets

(51) Int. Cl.
*A61N 5/10* (2006.01)
*G01T 1/22* (2006.01)
*G01T 1/29* (2006.01)

(52) U.S. Cl.
CPC ........ *G01T 1/29* (2013.01); *A61N 2005/1087* (2013.01)

(56) References Cited

FOREIGN PATENT DOCUMENTS

| | | |
|---|---|---|
| KR | 10-2012-0084591 | 7/2012 |
| KR | 10-2012-0085499 | 8/2012 |
| KR | 10-1320891 | 10/2013 |

* cited by examiner

DEVICE FOR DETECTING THERAPEUTIC PROTON BEAM EMITTED IN SCATTERING MODE

CROSS-REFERENCE TO RELATED APPLICATIONS

This application is a national phase application under 35 U.S.C. § 371 of International Application No. PCT/KR2014/012117 filed Dec. 10, 2014, which claims priority to Korean Patent Application No. 10-2013-0169318 filed Dec. 31, 2013. The contents of each of the above-referenced applications are incorporated into the present application by reference.

TECHNICAL FIELD

The present invention relates to a proton beam detection apparatus, and more particularly, to a proton beam detection apparatus including a sensor having optical fibers in an arrangement structure capable of accurately and efficiently detecting a proton dose distribution such as a Bragg peak, a spread out Bragg peak (SOBP), and the symmetry of a therapeutic proton beam emitted in a scattering mode.

BACKGROUND ART

Generally, various irradiation methods of transmitting a proton beam generated by an accelerator such as a cyclotron or a synchrotron to a patient for radiotherapy using protons have been used. One of general proton beam transmission methods which are currently being used most in proton-therapeutic institutions is a scattering mode in which a large therapeutic irradiation surface is formed by allowing protons to collide with a target of a certain material to be scattered.

Meanwhile, when a flux of a therapeutic proton beam source is incident on a patient, an absorbed dose changes according to depth. Since the change depends on many conditions such as energy and the depth of the flux, a distance from the beam source, etc., a dose of the patient may be calculated considering variations which have an effect on a dose distribution at a deep part. A basic step of a dose calculation method is setting a dose distribution at a deep part along a central axis of a flux. Such basic dose distribution materials may be measured using a small ion chamber detector at a water phantom with scattering properties very similar to the radiation absorption of general tissue and other soft tissue. However, since it is not always possible to put a radiation detector into water, a solid drying phantom which replaces water has been developed. Polymethyl methacrylate (PMMA, Lucite, Plexiglass) and polystyrene are mostly used as dose measurement phantoms. In the case of a water phantom, dose information is obtained at each position while an ion chamber detector is moved left, right, up, and down in a phantom. In the case of a solid phantom, since it is necessary to fix a measurement point as one point and to measure while changing a thickness of the phantom, a lot of measurement time is needed and efficiency decreases a lot.

Other than a method using an ion chamber detector, there is a method of measuring a dose using optical fibers. Korean Patent Publication No. 10-2012-0085499, a prior document, discloses a method of measuring a dose of a therapeutic proton beam using optical fibers. The method of measuring the dose of the proton beam disclosed in the prior document is a technology of measuring a dose distribution of a proton beam using optical fibers with different lengths in a water phantom. To apply the technology disclosed in the prior document to detect a therapeutic proton beam emitted in a scattering mode, it is necessary to move a position of the water phantom to detect a distance through which the proton beam emitted in the scattering mode passes and a dose for each position. Accordingly, since it is necessary to move the position of the water phantom in the technology disclosed in the prior document, a long measurement time is consumed and checking an accurate position is difficult which causes a large decrease in measurement efficiency.

DISCLOSURE

Technical Problem

The present invention provides an apparatus for detecting a therapeutic proton beam emitted in a scattering mode capable of improving accuracy in proton therapy by precisely detecting a position and a dose of the therapeutic proton beam emitted in the scattering mode.

Technical Solution

One aspect of the present invention provides an apparatus for detecting a therapeutic proton beam emitted from a scattering mode proton beam source, including a sensor which includes a plurality of detection modules each including a reference optical fiber and a detection optical fiber having a longer length than a length of the reference optical fiber. Here, the plurality of detection modules are diagonally arranged in a depth direction in which the proton beam emitted from the proton beam source progresses.

The sensor may include a plurality of diagonal arrangement structures each including a predetermined number of the detection modules arranged in the depth direction in which the proton beam emitted from the proton beam source progresses, and the diagonal arrangement structures may be repeatedly arranged in the depth direction in which the proton beam emitted from the proton beam source progresses.

The apparatus may further include an optical detector which detects light generated by the reference optical fiber and the detection optical fiber included in the sensor and outputs an electrical signal corresponding thereto and a signal processor which calculates an intensity of light corresponding to a difference in lengths of the detection optical fiber and the reference optical fiber for each detection module.

Another aspect of the present invention provides an apparatus for detecting a therapeutic proton beam emitted from a scattering mode proton beam source, including a sensor which includes a plurality of detection modules each including a reference optical fiber and a detection optical fiber having a longer length than a length of the reference optical fiber. Here, the plurality of detection modules are arranged in parallel at the same depth in a depth direction in which the proton beam emitted from the proton beam source progresses.

The plurality of detection modules each may include the reference optical fiber and two detection optical fibers which are disposed on both sides of the reference optical fiber and have lengths longer than the length of the reference optical fiber.

The apparatus may further include an optical detector which detects light generated by the reference optical fiber and the detection optical fiber included in the sensor and outputs an electrical signal corresponding thereto and a signal processor which calculates an intensity of light corresponding to a difference in lengths of the detection optical fiber and the reference optical fiber for each detection module.

Still another aspect of the present invention provides an apparatus for detecting a therapeutic proton beam emitted in a scattering mode proton beam source, including a first sensor which includes a plurality of first detection modules which each include a first reference optical fiber and a first detection optical fiber having a length longer than a length of the first reference optical fiber and diagonally arranged in a depth direction in which the proton beam emitted from the proton beam source progresses and a second sensor which includes a plurality of second detection modules which each include a second reference optical fiber and a second detection optical fiber having a length longer than a length of the second reference optical fiber and arranged in parallel at the same depth in the depth direction in which the proton beam emitted from the proton beam source progresses.

The first sensor may include a plurality of diagonal arrangement structures each including a predetermined number of the first detection modules arranged in the depth direction in which the proton beam emitted from the proton beam source progresses, and the diagonal arrangement structures may be repeatedly arranged in the depth direction in which the proton beam emitted from the proton beam source progresses.

The plurality of detection modules each may include the second reference optical fiber and two second detection optical fibers which are disposed on both sides of the second reference optical fiber and have lengths longer than the length of the second reference optical fiber.

The apparatus may further include a first optical detector which detects light generated by the first reference optical fiber and the first detection optical fiber included in the first sensor and outputs an electric signal corresponding thereto, a second optical detector which detects light generated by the second reference optical fiber and the second detection optical fiber included in the second sensor and outputs an electric signal corresponding thereto, and a signal processor which receives the electric signal output from the first optical detector, calculates an intensity of light corresponding to a difference in lengths of the first detection optical fiber and the first reference optical fiber for each of the first detection modules, receives the electrical signal output from the second optical detector, and calculates an intensity of light corresponding to a difference in lengths of the second detection optical fiber and the second reference optical fiber for each of the second detection modules.

Advantageous Effects

According to the present invention, a plurality of optical fibers for detecting a proton beam are arranged in a depth direction of a therapeutic proton beam emitted in a scattering mode, thereby quickly and efficiently detecting dose information (a Bragg peak or spread out Bragg peak (SOBP)) of the proton beam in the depth direction without moving a water phantom or a position of a sensor. Particularly, according to the present invention, spatial resolution of proton beam detection may be improved by applying two optical fibers having different lengths which form one detection module. Interference between the optical fibers, etc. may be excluded by diagonally arranging the detection module in the depth direction to further increase detection accuracy.

Also, according to the present invention, a plurality of optical fibers for detecting a proton beam are arranged at the same depth in a depth direction of a therapeutic proton beam emitted in a scattering mode, thereby quickly and efficiently detecting dose information (the symmetry) of the proton beam at the same depth without moving a water phantom or a position of a sensor. Particularly, according to the present invention, a detection module including three optical fibers in which two optical fibers and an optical fiber with shorter length than the two optical fibers and disposed therebetween are disposed is configured to detect light corresponding to length differences between the two optical fibers and the one optical fiber with the shorter length to generate detection values of two channels using one detection module, thereby reducing the number of optical fibers.

MODE FOR INVENTION

Hereinafter, embodiments of the present invention will be described in detail with reference to the attached drawings. However, the embodiments of the present invention may be modified into several different shapes and the scope of the present invention is not limited to the embodiments which will be described below. The embodiments of the present invention are provided to more completely explain the present invention to one of ordinary skill in the art of the present invention. Also, terms defined while describing the present invention are defined considering functions thereof in the present invention, which may vary according to the intention of those skilled in the art or conventions. Accordingly, the terms are not to be understood as meanings which limit the technical components of the present invention.

Figure 1:
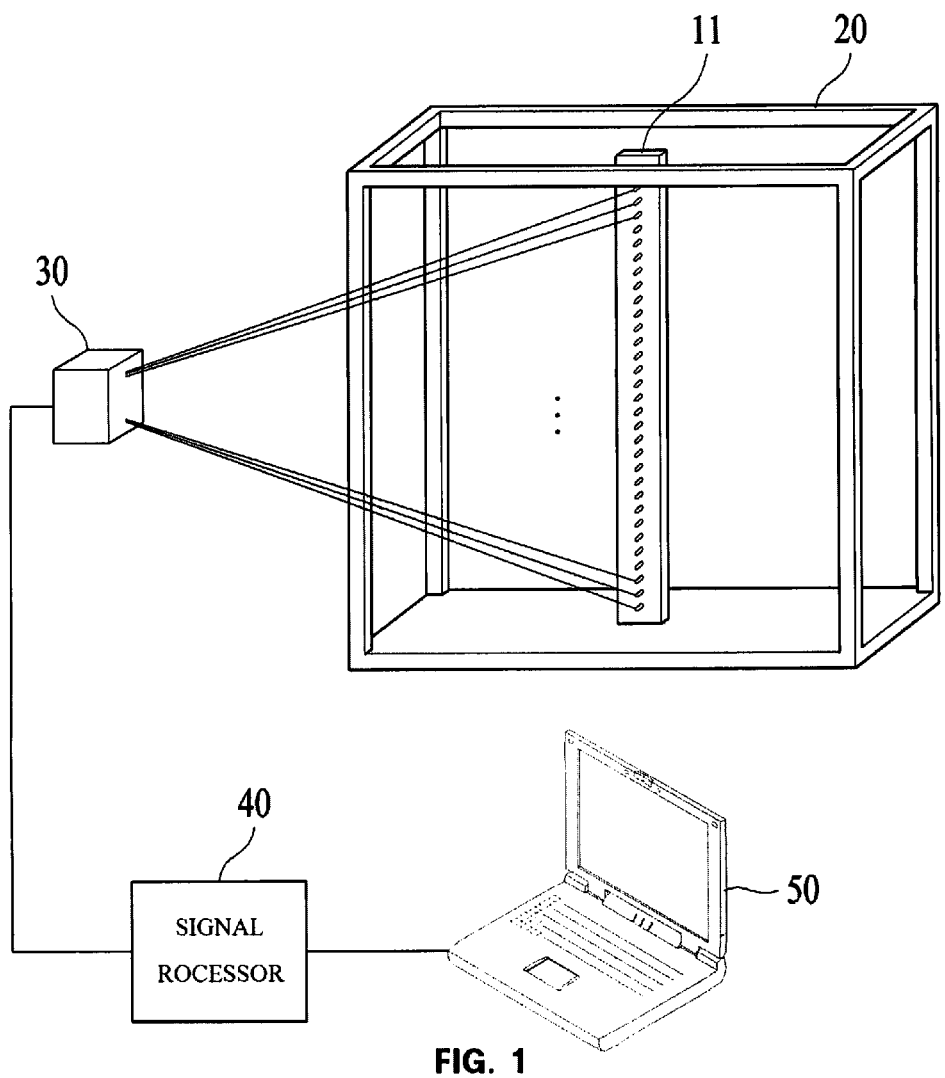
FIG. 1 is a configuration diagram of an apparatus for detecting a therapeutic proton beam emitted in a scattering mode according to one embodiment of the present invention.

FIG. 1 is a configuration diagram of an apparatus for detecting a therapeutic proton beam emitted in a scattering mode according to one embodiment of the present invention.

The apparatus for detecting the therapeutic proton beam emitted in the scattering mode according to one embodiment of the present invention shown in FIG. 1 is an embodiment having a sensor structure for detecting a distance from a proton beam source which emits the therapeutic proton beam in the scattering mode, that is, a proton dose according to a depth of the proton beam. A Bragg peak and a spread out Bragg peak (SOBP), which are analysis information in a depth direction of the proton beam source, may be calculated using the proton dose detected by the embodiment described above.

Referring to FIG. 1, the apparatus for detecting the therapeutic proton beam emitted in the scattering mode according to one embodiment of the present invention may include a sensor 11 which includes optical fibers, an optical signal detector 30 for detecting an optical signal generated by the optical fibers included in the sensor 11, a signal processor 40 which calculates a proton dose using information on the optical signal detected by the optical signal detector 30, and a display portion 50 for displaying a calculation result of the signal processor 40.

Figure 2:
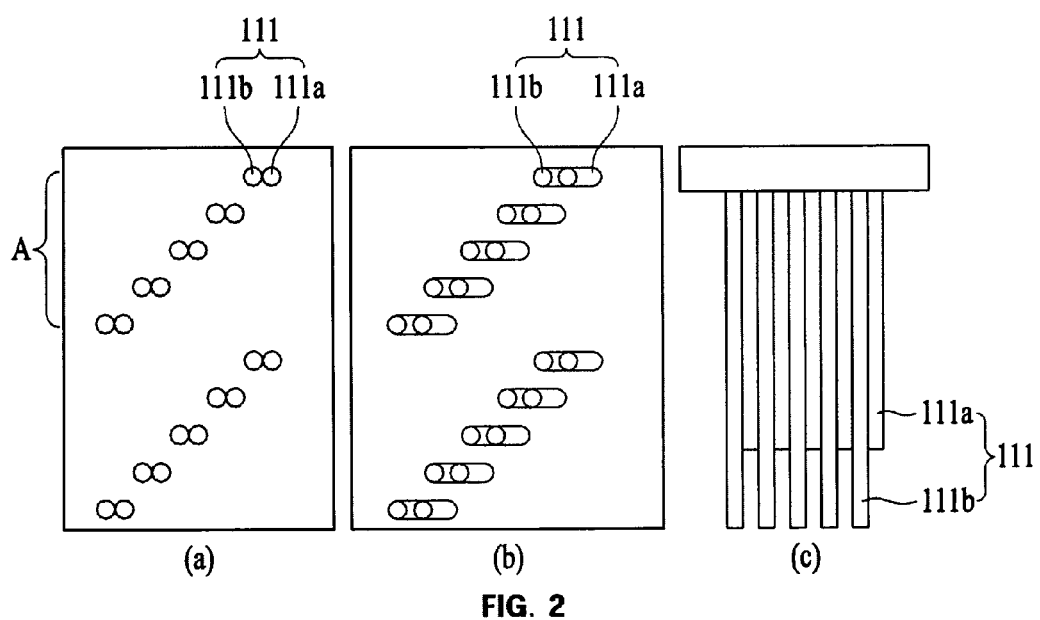
FIG. 2 is a view of a sensor of the apparatus for detecting the therapeutic proton beam emitted in the scattering mode according to one embodiment of the present invention shown in FIG. 1 in more detail.

FIG. 2 is a view of the sensor of the apparatus for detecting the therapeutic proton beam emitted in the scattering mode according to one embodiment of the present invention shown in FIG. 1 in more detail. Particularly, FIG. 2(a) is a front view, FIG. 2(b) is a perspective view, and FIG. 2(c) is a plane view.

Referring to FIG. 2, the sensor 11 may be disposed in a water phantom 20 and may include a plurality of optical fibers. Each of the plurality of optical fibers may have the following configuration. Two optical fibers 111a and 111b having different lengths form one detection module 111 for detecting a proton beam. The two optical fibers 111a and 111b which form the one detection module 111 are disposed at the same depth of the therapeutic proton beam emitted in the scattering mode. One optical fiber 111a is a reference optical fiber, and another optical fiber 111b is a detection optical fiber longer than the reference optical fiber 111a. The sensor 11 is configured to have a plurality of detection modules. The plurality of detection modules are diagonally arranged in a depth direction of the therapeutic proton beam emitted in the scattering mode. Also, a diagonal arrangement structure A including the plurality of detection modules may be repeatedly arranged in the depth direction of the therapeutic proton beam emitted in the scattering mode. The one detection module with the above structure may form one channel which outputs a result of detecting a proton beam at a corresponding depth.

The optical detector 30 may be a multi-channel optical detection apparatus which detects optical signals transmitted from the optical fibers 111a and 111b of the sensor 11 for each of the optical signals and converts a detection result into an electric signal to output. For example, the optical detector 30 may be embodied as a multi-anode photomultiplier tube (MAPMT) or a photodiode array.

The signal processor 40 may receive and process a light detection result transmitted from the optical detectors 30 to generate information on a proton beam position and a proton beam dose distribution. In more detail, the signal processor 40 may receive and convert the electrical signal generated by detecting light transmitted from the optical detector 30 into a digital signal and may calculate desired information (the proton beam position and/or the proton beam dose distribution) by processing the digital signal according to a preprogrammed routine. Generally, the signal processor 40 may be embodied as user-programmable data acquisition (DAQ).

In one embodiment of the present invention, the signal processor 40 may calculate levels of the optical signals detected by the detection module 111 including the reference optical fiber 111a and the detection optical fiber 111b and may determine the level of the optical signal from a portion of the detection optical fiber 111b which has a length longer than the reference optical fiber 11a to be a detection value of the corresponding detection module.

The display portion 50 is an element for receiving and visually displaying the information calculated by the signal processor 40 and may be embodied by a general computer system (a desktop personal computer (PC), a notebook PC, a tablet PC, etc.) The display portion 50 may not only display the information provided by the signal processor 40 but may also be an interface unit which may provide commands of a user for requesting, processing, and correcting programs and data to the signal processor 40.

Figure 3:
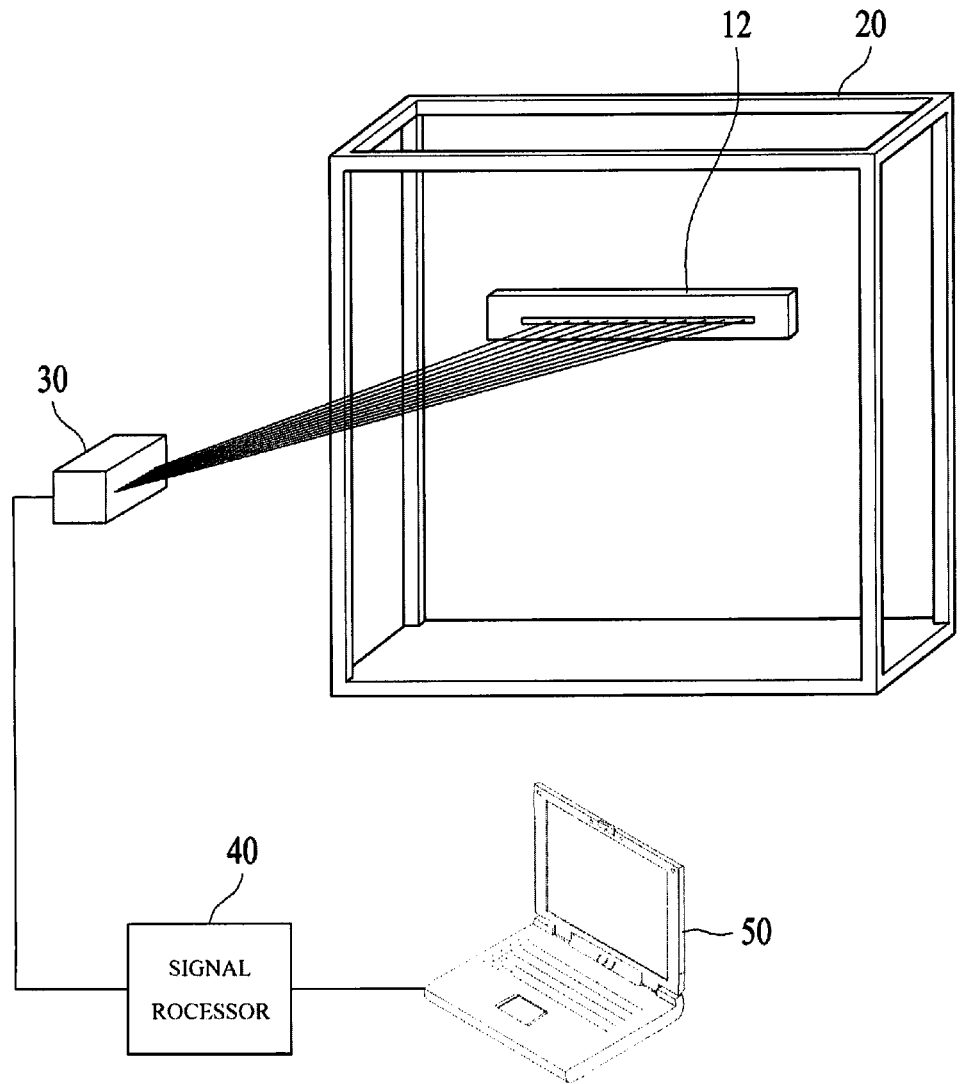
FIG. 3 is a configuration diagram of an apparatus for detecting a therapeutic proton beam emitted in a scattering mode according to another embodiment of the present invention.

FIG. 3 is a configuration diagram of an apparatus for detecting a therapeutic proton beam emitted in a scattering mode according to another embodiment of the present invention.

The apparatus for detecting the therapeutic proton beam emitted in the scattering mode according to the embodiment of the present invention shown in FIG. 3 is an embodiment having a sensor structure for detecting a proton dose according to a position at the same depth from a proton beam source which emits the therapeutic proton beam in the scattering mode. A detection value for checking the symmetry of the proton beam source may be obtained using the proton dose detected according to the embodiment.

Referring to FIG. 3, the apparatus for detecting the therapeutic proton beam emitted in the scattering mode according to another embodiment of the present invention may include a sensor 12 which includes optical fibers, the optical signal detector 30 for detecting an optical signal generated by the optical fibers included in the sensor 12, the signal processor 40 which calculates a proton dose using information on the optical signal detected by the optical signal detector 30, and the display portion 50 for displaying a calculation result of the signal processor 40.

Figure 4:
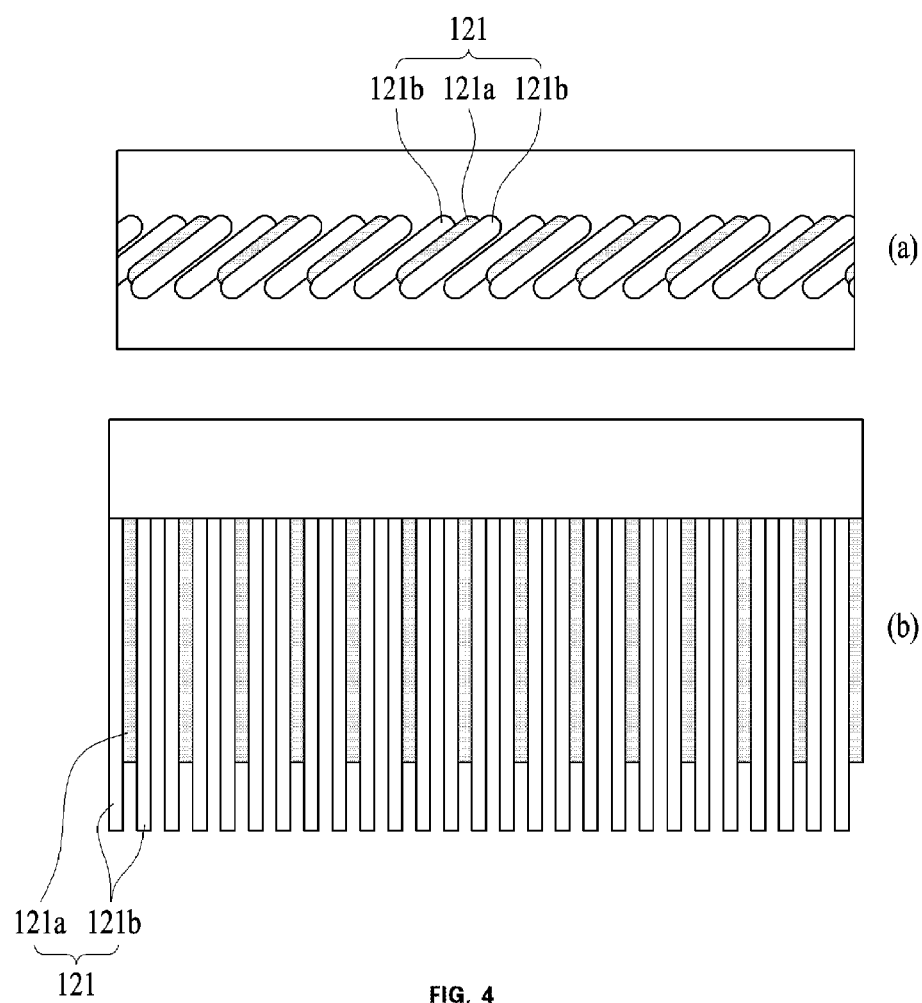
FIG. 4 is a view of a sensor of the apparatus for detecting the therapeutic proton beam emitted in the scattering mode according to another embodiment of the present invention shown in FIG. 3 in more detail.

FIG. 4 is a view of the sensor of the apparatus for detecting the therapeutic proton beam emitted in the scattering mode according to another embodiment of the present invention shown in FIG. 3 in more detail. Particularly, FIG. 4(a) is a perspective view and FIG. 4(b) is a plane view.

Referring to FIG. 4, the sensor 12 may be disposed in the water phantom 20 and may include a plurality of optical fibers. Each of the plurality of optical fibers may have a following configuration. Two optical fibers 121b having the same lengths and one optical fiber 121a having a length different from the optical fibers 121b form one detection module 121 for detecting a proton beam. The three optical fibers 121a and 121b which form the one detection module 121 are disposed at the same depth of the therapeutic proton beam emitted in the scattering mode. The one optical fiber 121a becomes a reference optical fiber, and other optical fibers 121b are detection optical fibers longer than the reference optical fiber 121a. The sensor 12 is configured to have a plurality of detection modules. The plurality of detection modules are diagonally arranged at the same depth of the therapeutic proton beam emitted in the scattering mode. In this embodiment, one detection module outputs a two channel detection result. This will be described below.

Since the optical detector 30, the signal processor 40, and the display portion 50 are substantially identical to the embodiment shown in FIG. 1, a detailed description thereof will be omitted. However, in the embodiment in FIGS. 3 and 4, the signal processor 40 may calculate levels of the optical signals detected by the detection module 121 including the reference optical fiber 121a and the detection optical fibers 121b and may determine levels of the optical signals from portions of the detection optical fibers 121b which have lengths longer than the reference optical fiber 121a to be a detection value of the corresponding detection module.

Hereinafter, an operation and effect of the apparatus for detecting the therapeutic proton beam emitted in the scattering mode according to one embodiment of the present invention will be described in detail with reference to the attached drawings.

First, the embodiment of the present invention shown in FIGS. 1 and 2 will be described.

In the embodiment of FIG. 1, the proton beam source which emits the therapeutic proton beam emitted in the scattering mode is located above the water phantom 20 and emits a proton beam toward the water phantom. In one embodiment of the present invention, the sensor 11 is disposed to detect a dose in a depth direction in which the proton beam progresses. For this, the sensor 11 includes the plurality of optical fibers arranged in the depth direction. Particularly, the optical fibers are configured as the plurality of detection modules each including two optical fibers 111a and 111b having different lengths and has a structure in which the plurality of detection modules are diagonally arranged in the depth direction. As described above, in one embodiment of the present invention, the optical fibers are diagonally arranged in the depth direction, thereby reducing an effect caused by interruption between optical fibers and a scattering thereof.

When the proton beam emitted from the proton beam source disposed above the water phantom 20 passes through the plurality of optical fibers 111a and 111b, photons are generated by the Cherenkov radiation effect in the optical fibers. That is, light may be generated at the optical fiber through which the proton beam passes.

The Cherenkov radiation effect is an effect in which photons (light) are generated in a conic shape having a certain angle with an incident beam when a charged particle penetrates a medium at a speed faster than that of light in a medium and is generated by a charged particle with a certain level of energy or more. In more detail, high energy secondary electrons (177 KeV or more) which are released due to reactions between protons and the optical fibers emit Cherenkov photons in a disk. Generally, Cherenkov photons are emitted as ultraviolet (UV) rays in an area of 200 nm and may have a wavelength band across almost the whole visible area. Here, since a release probability of Cherenkov light is inversely proportional to the square of a wavelength, the largest number of photons is released at a wavelength band of a UV area. Accordingly, in one embodiment of the present invention, to increase photo detection efficiency, optical efficiency may be increased by manufacturing the optical detector 30 more sensitive to UV rays.

An intensity of the optical signal generated by the optical signal is detected by the optical detector 30 and is generated as an electric signal corresponding thereto. The electric signal includes information on an amount of light (the intensity of light) further detected by the optical detector 30 and is provided to the signal processor 40. The signal processor 40 may calculate a value corresponding to the intensity of light generated from a difference in lengths of the two optical fibers included in each detection module for each detection module and may calculate a proton dose according to a depth using the intensity of the light. The proton dose obtained by the signal processor 40 is provided to the display portion 50 and visually displayed. A PC which embodies the display portion 50 may generate other information for checking a proton beam distribution through another calculation.

In one embodiment of the present invention, the one detection module including the two optical fibers 111a and 111b having different lengths may output two optical signals generated by the respective optical fibers as the proton beam passes. Since the two optical fibers 111a and 111b have different lengths, intensities of the optical signals output therefrom are different. Accordingly, when a difference between the intensity of the optical signal output from the detection optical fiber 111b and the intensity of the optical signal output from the reference optical fiber 111a is obtained, an intensity of the optical signal output from the portion corresponding to the difference in lengths of the two optical fibers may be obtained. A therapeutic proton beam emitted in a secondary scattering mode generally has a field size of 10 to 25 cm. However, since all optical fibers in the field are included in an active area, spatial resolution decreases when one optical fiber is used. To solve the problem, according to the present invention, two optical fibers form one detection module and an intensity of an optical signal corresponding to a difference in lengths of the two optical fibers is used, thereby improving spatial resolution. As the difference in lengths of the two optical fibers decreases, the spatial resolution may be further improved.

Next, the embodiment of the present invention shown in FIGS. 3 and 4 will be described.

Like the embodiment of FIGS. 1 and 2 described above, in the embodiment of FIG. 3, the proton beam source which emits the therapeutic proton beam emitted in the scattering mode is located above the water phantom 20 and emits a proton beam toward the water phantom. In another embodiment of the present invention, the sensor 12 is disposed to detect a dose at a position having the same depth in a depth direction in which the proton beam progresses. For this, the sensor 12 includes the plurality of optical fibers aligned at the same depth. Particularly, the two optical fibers 121b having the same lengths and the one optical fiber 121a having a length different from the optical fibers 121b form the one detection module 121 for detecting a proton beam. The reference optical fiber 121a among the optical fibers 121a and 121b which form the one detection module 121 may be disposed between the detection optical fibers 121b having longer lengths. As described above, the one detection module includes the one reference optical fiber 121 and the two detection optical fibers 121b to allow the one detection module to generate a two channel optical signal corresponding to a difference between the lengths of the reference optical fiber 121a and the detection optical fiber 121b, thereby reducing the number of the reference optical fibers 121a. Since it is identical the above description of the embodiment of FIGS. 1 and 2 to generate light by detecting a proton beam at an optical fiber, a repetitive description thereof will be omitted.

An intensity of the optical signal generated by the optical signal is detected by the optical detector 30 and is generated as an electric signal corresponding thereto. The electric signal includes information on an amount of light (the intensity of light) further detected by the optical detector 30 and is provided to the signal processor 40. The signal processor 40 may calculate a two channel detection value corresponding to the intensity of light generated from a difference in the lengths of the one optical fiber and the two optical fibers included in the detection module and may calculate a proton dose according to a depth using the intensity of the light. The proton dose obtained by the signal processor 40 is provided to the display portion 50 and visually displayed. A PC which embodies the display portion 50 may generate other information for checking proton beam distribution through another calculation.

Meanwhile, although not shown in the drawings, still another embodiment of the present invention may be embodied to dispose the sensor structures of FIG. 1 and FIG. 3 in one water phantom. In this case, one optical detector which detects light at the optical fibers of the sensor 11 shown in FIGS. 1 and 2 and another optical detector which detects light at the optical fibers of the sensor 12 shown in FIGS. 3 and 4 may be provided and the signal processor 40 may receive and process an electric signal corresponding to the light detected from the two optical detectors.

As described above, according to the present invention, a plurality of optical fibers for detecting a proton beam are arranged in a depth direction of a therapeutic proton beam emitted in a scattering mode, thereby quickly and efficiently detecting dose information (A Bragg peak or SOBP) of the proton beam in the depth direction without moving the water phantom or a position of a sensor. Particularly, spatial resolution of proton beam detection may be improved by applying two optical fibers having different lengths which form one detection module. Interference between the optical fibers, etc. may be excluded by diagonally arranging the detection module in the depth direction to further increase detection accuracy.

Also, according to the present invention, a plurality of optical fibers for detecting a proton beam are arranged at the same depth in a depth direction of a therapeutic proton beam emitted in a scattering mode, thereby quickly and efficiently detecting dose information (a symmetry) of the proton beam at the same depth without moving a water phantom or a position of the sensor. Particularly, a detection module including three optical fibers in which two optical fibers and an optical fiber with a shorter length than the two optical fibers and disposed therebetween are disposed is configured to detect light corresponding to length differences between the two optical fibers and the one optical fiber with the shorter length to generate a two channel detection value using one detection module, thereby reducing the number of optical fibers.

Although a few embodiments of the present invention have been shown and described, it should be appreciated by those skilled in the art that changes may be made in these embodiments without departing from the principles and spirit of the invention, the scope of which is defined in the claims and their equivalents.

The invention claimed is:

1. An apparatus for detecting a therapeutic proton beam that is emitted in a scattering mode from a proton beam source and progresses in a first direction that is a depth direction, comprising:
   a first sensor which comprises a plurality of first detection modules each comprising a first reference optical fiber and a first detection optical fiber having a length longer than a length of the first reference optical fiber, wherein the plurality of first detection modules each are disposed from each other along the first direction and diagonally arranged so that the adjacent first detection modules are not to overlap with each other in the first direction; and
   a second sensor which comprises a plurality of second detection modules each comprising a second reference optical fiber and two second detection optical fibers having a length longer than a length of the second reference optical fiber, wherein the plurality of second detection modules are each arranged in parallel at the same depth in the depth along a second direction, which is orthogonal to the first direction,
   wherein the first reference optical fiber and the first detection optical fiber in the first detection modules each have the same depth, and
   wherein the second detection module each comprise the two second detection optical fibers which are disposed on both sides of the second reference optical fiber and generate two channels.

2. The apparatus of claim 1, wherein the first sensor comprises a plurality of diagonal arrangement structures each comprising a predetermined number of the first detection modules arranged in the first direction in which the proton beam emitted from the proton beam source progresses, and
   wherein the diagonal arrangement structures are repeatedly arranged in the depth direction in which the proton beam emitted from the proton beam source progresses.

3. The apparatus of claim 1, further comprising:
   a first optical detector which detects light generated by the first reference optical fiber and the first detection optical fiber included in the first sensor and outputs an electric signal corresponding thereto;
   a second optical detector which detects light generated by the second reference optical fiber and the second detection optical fiber included in the second sensor and outputs an electric signal corresponding thereto; and
   a signal processor which receives the electric signal output from the first optical detector, calculates an intensity of light corresponding to a difference in lengths of the first detection optical fiber and the first reference optical fiber for each of the first detection modules, receives the electrical signal output from the second optical detector, and calculates an intensity of light corresponding to a difference in lengths of the second detection optical fiber and the second reference optical fiber for each of the second detection modules.

* * * * *